United States Patent
Yu et al.

(10) Patent No.: US 8,020,444 B2
(45) Date of Patent: Sep. 20, 2011

(54) FUNCTIONAL ACTUATOR-SENSOR PATH OPTIMIZATION IN STRUCTURAL HEALTH MONITORING SYSTEM

(75) Inventors: Zengpin Yu, Palo Alto, CA (US); Bao Liu, Cupertino, CA (US); Shawn J. Beard, Livermore, CA (US); David C. Zhang, Santa Clara, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 771 days.

(21) Appl. No.: 12/103,562

(22) Filed: Apr. 15, 2008

(65) Prior Publication Data

US 2008/0253231 A1      Oct. 16, 2008

Related U.S. Application Data

(60) Provisional application No. 60/912,112, filed on Apr. 16, 2007.

(51) Int. Cl.
*G01N 9/24* (2006.01)
(52) U.S. Cl. .......................................................... 73/601
(58) Field of Classification Search ........................ None
See application file for complete search history.

(56) References Cited

U.S. PATENT DOCUMENTS

2007/0018083 A1*   1/2007   Kumar et al. ............ 250/227.14

* cited by examiner

*Primary Examiner* — Robert Raevis
(74) *Attorney, Agent, or Firm* — Innovation Counsel LLP

(57) ABSTRACT

A method for optimizing transducer performance in an array of transducers in a structural health monitoring system includes specifying a plurality of paths between pairs of the transducers on a monitored structure and evaluating the quality of signal transmissions along the paths so as to optimize the gain and frequency operating condition of the transducers.

19 Claims, 4 Drawing Sheets

FUNCTIONAL ACTUATOR-SENSOR PATH OPTIMIZATION IN STRUCTURAL HEALTH MONITORING SYSTEM

RELATED APPLICATIONS

This application claims the benefit of U.S. Provisional Patent Application Ser. No. 60/912,112, filed Apr. 16, 2007, the entire disclosure of which is incorporated herein by reference.

BRIEF DESCRIPTION OF THE INVENTION

This invention relates generally to structural health monitoring (SHM) systems. More specifically, this invention relates to a methodology for selecting and optimizing functional actuator-sensor paths in such systems.

BACKGROUND

When a large area of a composite structure is monitored by a SHM system, a network of a large number of transducers may be used for that purpose. The transducers may be acoustic wave emitters ("actuators") and/or detectors ("sensors"). These transducers may form combinations of actuator-sensor paths that are many times more numerous than the total number of transducers in the array. It is very common for a transducer network to produce hundreds to thousands of signals in each scan of the plurality of possible paths.

Because of the differences that may occur among the path lengths and the paths due to the surrounding geometry and the possible diversity of sensor installation, the signals of different paths typically vary in quality. Signals of some paths may be too weak to provide reliable information about a region of the structure through which the acoustic wave signal passes. The signal energy and the optimal frequencies along different paths are typically also very different.

To ensure the quality of the signals and the accuracy of the subsequent signal processing for damage detection, it is desirable to pre-process the network signals and optimize the operational excitation-detection conditions. However, in systems with a large number of such signals, it may be impractical to perform this pre-processing manually. An automatic pre-processing method is therefore needed.

SUMMARY

In accordance with the present disclosure, a method is provided for automatically pre-processing signals obtained in a network of transducers of a SHM system.

In one embodiment, the pre-processing method processes detected acoustic wave signals received at a plurality of sensors, wherein the signals are characterized at least by amplitude and frequency. The method includes an auto-gain process, in which a transmit and a receive gain amplification is determined for each path for the frequency of the signal, and a frequency selection process for selecting the frequency providing the most sensitivity (e.g., amplitude and dynamic range).

The novel method further includes removing from the network those paths for transmitting and receiving signals in which the signals are disposed below a selected set of parameter threshold values, including signal strength and/or signal-to-noise ratio (SNR).

A better understanding of the above and many other features and advantages of the novel method of the present disclosure may be obtained from a consideration of the detailed description of some example embodiments thereof below, particularly if such consideration is made in conjunction with the several views of the appended drawings, wherein like elements are referred to by like reference numerals throughout.

DETAILED DESCRIPTION

Figure 1:
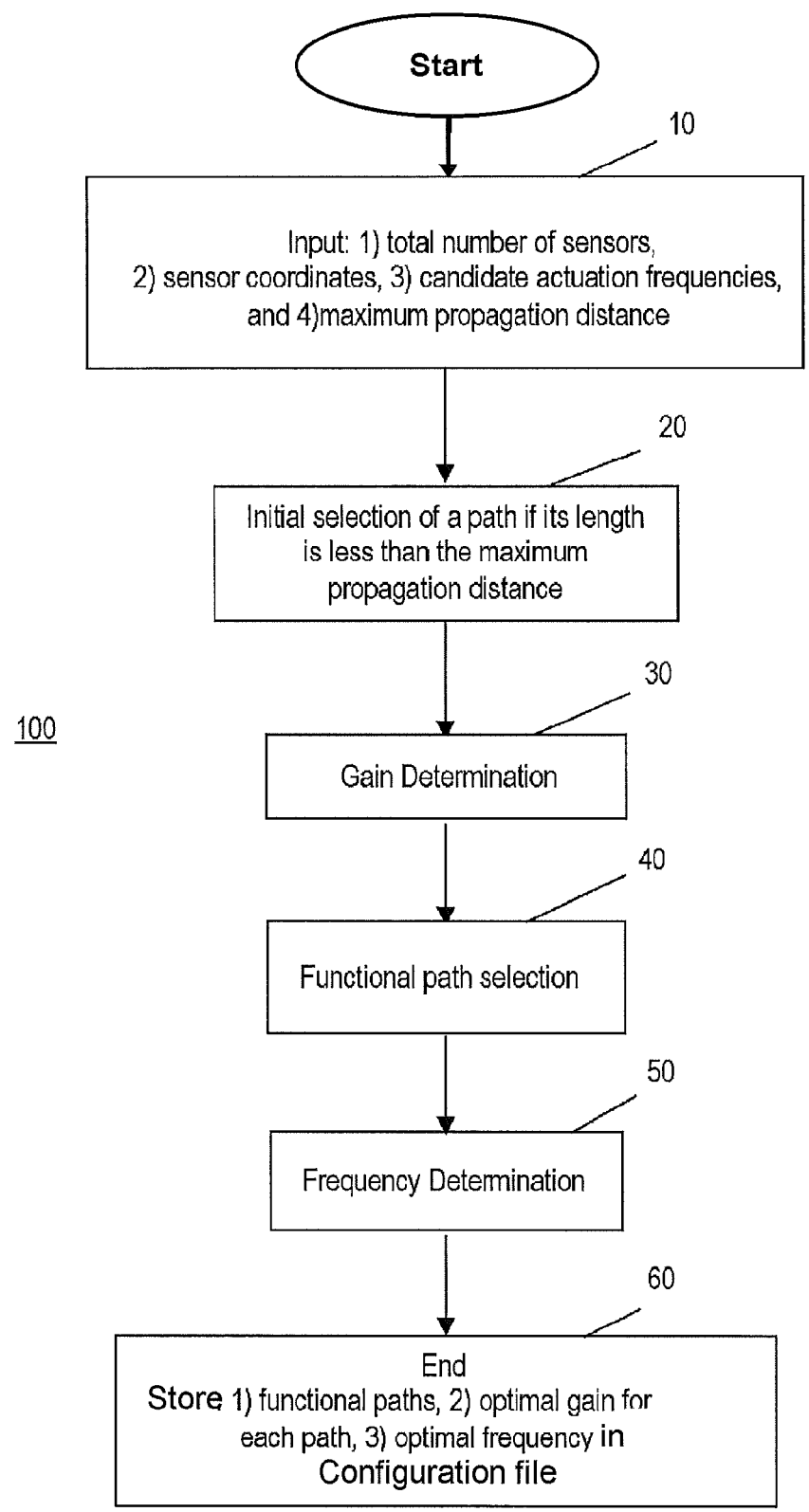
FIG. 1 is a process flow diagram of an example embodiment of a method for optimizing actuator-sensor path signals in a SHM system in accordance with the present disclosure.

FIG. 1 is a process flow diagram of an example embodiment of a method 100 for optimizing actuator-sensor path signals of a SHM system, which may be executed the first time a sensor network is used, or periodically thereafter when the system is calibrated. This method includes, at step 10, 1) specifying a sensor network, including the total number and 2) the respective location coordinates of all of the transducers applied to a structure that is to be inspected and monitored by the system. Initial step 10 also includes specifying 3) candidate actuation signal frequencies for each actuator-sensor path of the network and 4) a maximum allowable signal propagation distance for transmission of acoustic wave signals in or on the surface of the structure.

At step 20 of the example method 100, physical interrogation of the network of sensors is begun to select an initial set of paths between sensors on the structure. The initial selection of paths is made on the basis of the maximum signal propagation distance provided at step 10. That is, only those signal paths between respective actuator-sensor pairs of the array having a length less than or equal to the maximum allowable signal propagation distance are selected for optimization.

At step 30 of the exemplary method 100, a gain determination analysis is then performed for each selected path, including the removal of electromagnetic interference (EMI) cross-talk from the signals, and the selecting of an optimum amplification gain (both in transmit and receive). Different paths may have the same or different amplification gains.

At step 40, a determination is made of which of the paths of the initial set are "functional," i.e., which of the paths have signals of sufficient amplitude and SNR to be useful for monitoring of the structure. Criteria for selecting functional paths include specifying a minimum threshold for signal strength and SNR. The functional path selecting step 40 then removes all other paths, i.e., those deemed to be non-functional, from the set of selected paths.

After the functional paths of the system are determined, at step 50, a frequency determination analysis is performed for each functional path to determine at what frequency the actuator-sensor path monitoring is to be effected. This analysis includes selecting the most sensitive frequency response for each path. Different paths may have the same or different frequencies.

At step 60 of the method 100, an output to a configuration file is provided, including 1) the specification of the functional paths, 2) the corresponding optimal gains (i.e., transmit and receive) of the paths, and 3) the optimal operating frequencies for each path.

As those of skill in the art will appreciate, in each of the gain determination step 30, the functional path selection step 40 and the optimal frequency determination step 50 of the example method 100 of FIG. 1, an evaluation of the signal quality (Q) of the detected signal is strongly indicated. One or more signal features may require measuring to describe the signal quality. Such measuring may include, in gain analyzing, a measured maximum signal amplitude after cross-talk is removed; a measured total energy in the whole signal of the acoustic pulse corresponding to the "first arrival" signal (i.e., the signal corresponding to a direct path transmission between the actuator and the sensor for a selected path); a measured or estimated SNR (whether an amplitude, energy or power ratio); and, a measure of "robustness" to environmental change, wherein, for example, such robustness may be defined as R=1/variance of the measured signal energy while an environmental effect, such as temperature, changes within a specified range. For example, if signal energy measured on a selected path remains within a specified range, the variance of the energy measured will be below a selected maximum threshold value, and the robustness R will exceed a minimum threshold value, indicating that the signal quality Q is satisfactory over the range of environmental variation. The signal energy may also be required, either individually or in correspondence with satisfying the robustness threshold R, to satisfy a specified SNR threshold.

Figure 2:
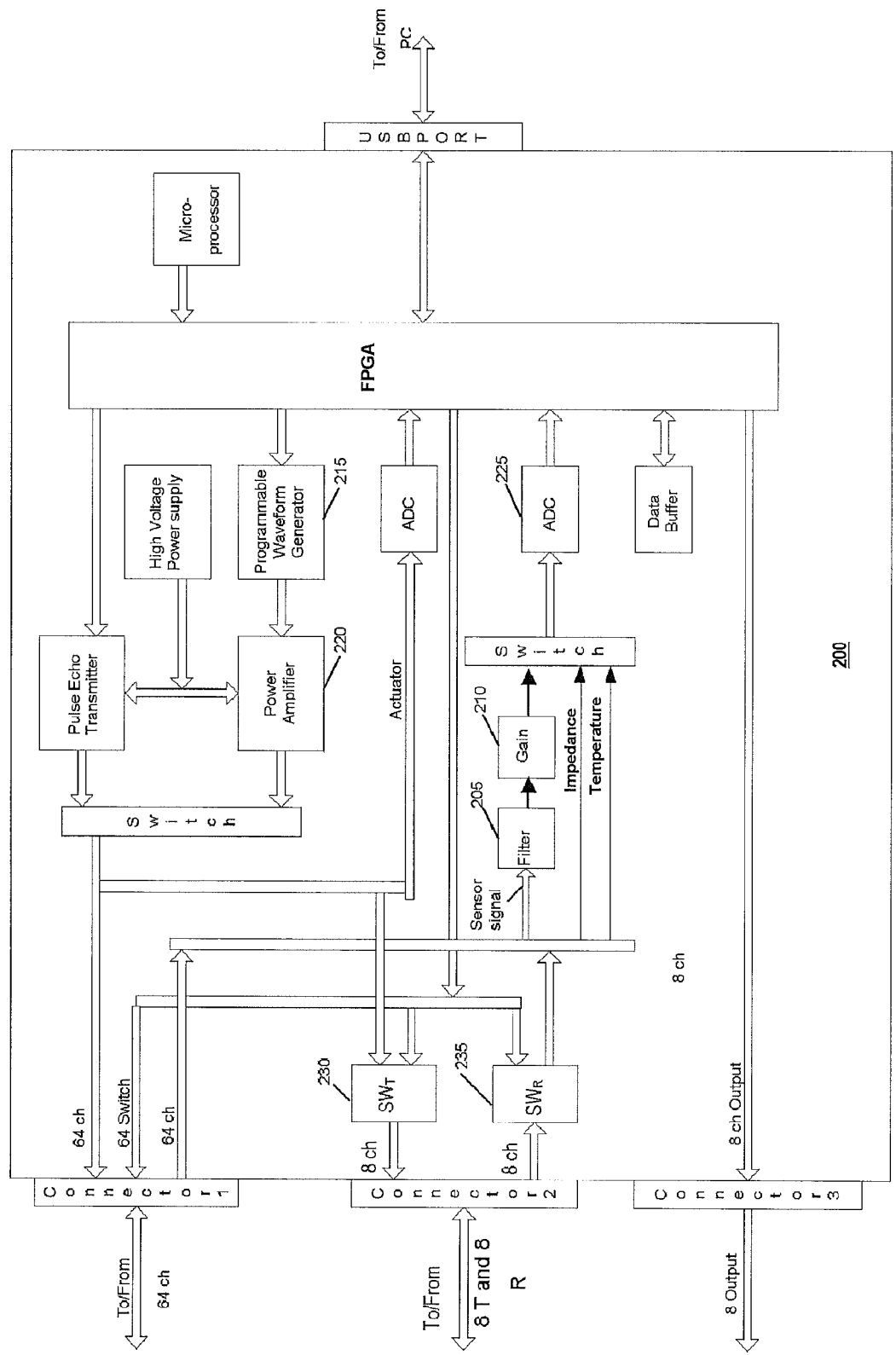
FIG. 2 is a functional block diagram of an example embodiment of a sensor array data acquisition and processing system in accordance with the disclosure.

The following discussion of the gain determination analysis step 30 of the example method 100 of FIG. 1 is made with reference to FIG. 2, which is a functional block diagram of an example sensor array data acquisition and processing system 200. The sensors of the array may comprise, for example, acoustic wave transducers, such as piezoelectric lead-zirconate-titanate (PZT) ceramic transducers. The acquisition and processing system 200 of FIG. 2 may include a signal receiver filter 205 and receiver gain block 210. The receiver filter 205 and receiver gain 210 provide analog filtering and variable gain to received signals before the signals are digitized. The range of variable gain supplied by the gain block may be, for example, 0 dB to 40 dB. A transmit gain block includes a programmable waveform generator 215, which provides an arbitrary waveform to a power amplifier 220 capable of outputting high voltage pulses to the PZT transducers. The power amplifier 220 may have a fixed gain. Thus, the transmit gain may be determined by the programmable waveform generator. Alternatively, the power amplifier 220 may have variable, programmable gain.

The receiver filter 205 and gain block 210 and the transmit gain block (i.e., the waveform generator 215 and power amplifier 220) may be applied in a coordinated manner to determine an optimal transmit gain and receive gain condition, where the optimal condition may be specified by requiring that the received RF signal envelope input to the analog to digital converter ADC 225 following the analog receiver filter 205 and gain block 210 does not saturate the ADC 225.

Filter/Gain Initialization

Figure 3:
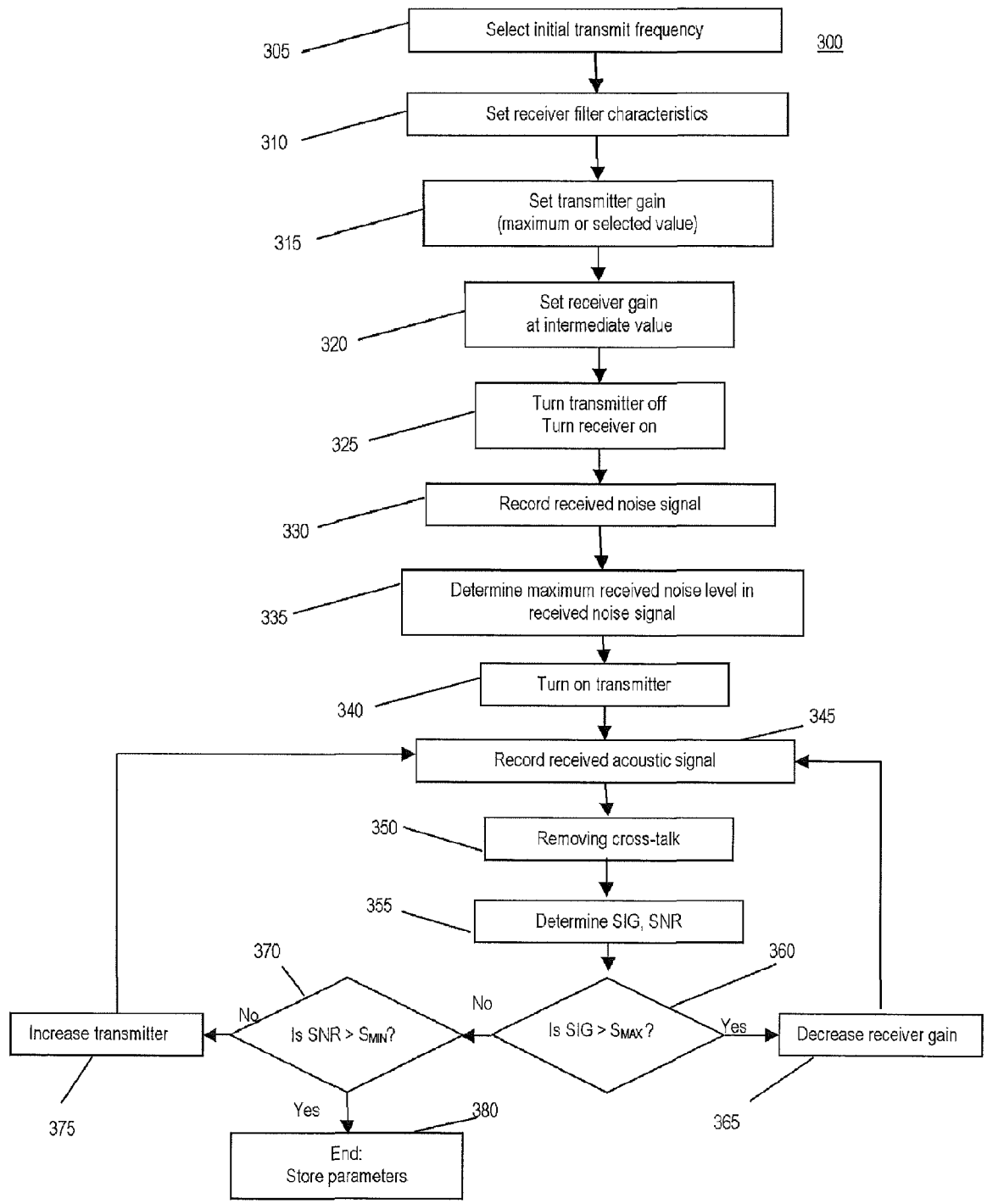
FIG. 3 is a process flow diagram of an example embodiment of an adaptive method for determining optimal transmit and receive conditions in a SHM system in accordance with the disclosure; and, FIG. 4 is a process flow diagram of an example embodiment of a method for frequency selection for an array of actuator-sensor paths in a SHM system in accordance with the disclosure.

As illustrated in FIG. 3, in one embodiment, an adaptive method 300 for determining the optimal transmit and receive conditions for each signal path at each actuation frequency includes initializing the receive filter 205, the transmit gain and the receive gain 210. Based on selecting an initial transmit frequency (step 305), the receive filter 205 may be initialized (step 310) to a matched filter characteristic, where the initial transmit frequency may be selected one by one from the candidate frequencies (step 10 of method 100 above) for the respective signal path. The transmit gain 210 may be set initially at the maximum possible value (step 315). Alternatively, transmit gain may be set at a user selected value. The receive gain may be set at a desired selected value (step 320), e.g., a gain intermediate the minimum and maximum gain values.

Receive Amplifier Gain Setup

In FIG. 3, an initial or desired variable gain is input to set the analog receive amplifier to a selected receive gain (step 320).

Noise Level Determination

Following initializing of the receiver filter (step 310) and transmitter gain (step 315) and receiver gain (step 320) above, the method 300 proceeds to determine the noise level in the receiver section of the acquisition and processing system 200 of FIG. 2. A transmit switch $SW_T$ 230 may be turned off while the receive block switch $SW_R$ 235 is on (step 325), i.e., the receiver block is in communication with a receive transducer for a selected path. The received signal is noise, and may be digitized and stored to a memory for analysis (step 330). The maximum received digitized signal amplitude is defined (step 335) as the maximum filtered, amplified and digitized received system noise for the receive gain setting.

Signal Level Determination

With the receive switch $SW_R$ 235 on, the transmit switch $SW_T$ 230 may be turned on (step 340), i.e., the transmit block is placed in communication with a transmit transducer, and an acoustic signal is transmitted for detection by the receive transducer and receive block of the system 200. The received analog filtered and gain amplified signal may be digitized and stored to the memory for analysis (step 345).

Preferably, cross-talk is removed from the signal (step 350). Cross-talk may be caused by EMI from direct radiation associated with the high voltage that may be required for actuators to excite the acoustic wave signals. The acoustic wave signals may be transmitted as packets, or pulses. Cross-talk may significantly affect the accuracy of detecting the arrival of acoustic pulses at the sensor transducers, and consequently, also affect the detection of damage. Therefore, removal of cross-talk from the signal is an important step.

Since the time of arrival of cross-talk is substantially instantaneous, various methods of time gating may be used for accomplishing this step. For example, in a digitized signal waveform, assuming the signal pulse length (taking into account the ring-down from the transducer) is shorter than the shortest time of arrival, digital signal processors, such as may be found in digital oscilloscopes, may be set to null all values of the digital signal waveform from the time corresponding to the trigger point to a time equal to or greater than the pulse length. Requiring the signal pulse length (and ring-down time) to be less than the shortest time of arrival insures that the cross-talk signal will not overlap the elastic wave signal, and cross-talk removal is thereby more easily facilitated.

The signal level SIG may be defined as the maximum received signal amplitude after removing the cross-talk corresponding to the current selected receive gain value. The SIG level may result in saturation of the input to the ADC 225 if it exceeds a maximum limiting value, $SIG_{MAX}$. If the received signal level SIG exceeds $SIG_{MAX}$, the receive gain may be reduced, e.g., by reducing the variable gain level. If the receive gain is already reduced to the minimal value and SIG still exceeds $SIG_{MAX}$, then the transmit gain may be reduced until SIG is at an acceptable level.

In the example method 300, SIG is also compared to the receiver noise level to compute a signal-to-noise ratio (SNR).

Both SIG and SNR may be determined (step 355) and the results used to adjust transmitter and receiver gains, in the following manner. If SIG exceeds $SIG_{MAX}$ (a "Yes" result in decision block 360) the receiver gain can be reduced (step 365), and a new signal transmitted. Recording of a new acoustic signal may be obtained by continuing at step 345. If SIG is less than $SIG_{MAX}$ (a "No" result in decision block 360), then the signal may be determined not to have reached a saturation level, and is then tested for SNR (decision block 370). If the SNR does not exceed a minimum selected value, e.g., $SNR_{MIN}$=20 dB (a No result in decision block 370), the transmitter gain can be increased (step 375) and the new acoustic signal obtained by continuing at acoustic signal record step 345. If the SNR is greater than $SNR_{MIN}$ (a Yes result in decision block 380), the example method 300 ends and the gain and frequency parameters for the selected path are stored (step 380).

The transmitter and receiver gain may now be considered correctly set, and initializing may proceed with selecting functional paths for all the candidate frequencies by comparing the signal with a minimum threshold for signal strength and/or SNR.

Determining Optimal Frequency

Since different paths may be sensitive to different actuation frequencies, it is desirable that different actuation frequencies be used for different paths. Alternatively, using an identical actuation frequency for all paths is computationally more efficient. A reasoning process in damage detection may allow use of both frequency selections depending on user specification or a threshold requirement.

Figure 4:
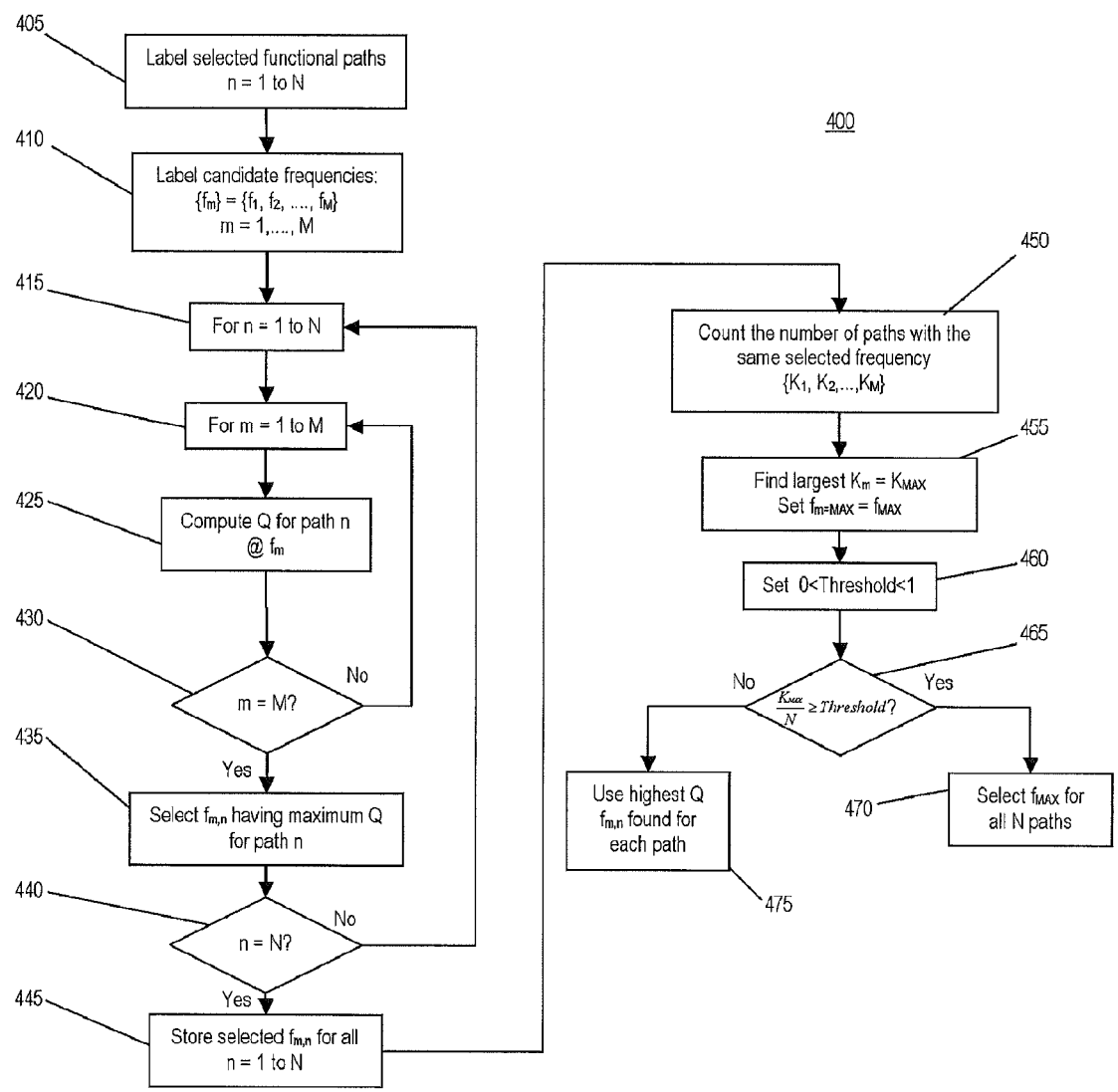

FIG. 4 is a process flow diagram of an example embodiment of a method 400 for selecting operating frequencies for an array of actuator-sensor paths in an example SHM system. Let N be the total number of paths 1, ... n, ... N selected (step 405). Let Q be a measure of signal quality. Let $\{f_1, f_2, \ldots, f_M\}$ (or, for convenience, denoted by $\{f_m\}$) be a set of M candidate frequencies for each actuator-sensor acoustic transmission path (step 410), where the number of candidate frequencies M for each path may be different depending on the selection of functional paths (step 40 of method 100 of FIG. 1). As indicated above, examples of Q that may be used to select frequency include, but are not limited to, a measured total signal energy, a measured or estimated signal-to-noise ratio, or a measure of robustness to environmental parameter changes.

As illustrated in FIG. 4, a pseudo-code for selection of different best suitable frequencies for different paths is:

| | |
|---|---|
| For n = 1 to N; | (1st loop starts at step 415) |
| For m = 1 to M; | ($2^{nd}$ loop starts at step 420) |
| Compute Q for the signal of the nth path at frequency $f_m$; | (step 425) |
| End m loop; | (step 430) |
| Find the maximum Q for the nth path; | (step 435) |
| End n loop; | (step 440) |
| Select the frequency that produces the maximum Q as the best suitable frequency for a path; | (step 445) |
| Store the selected frequencies. | (step 445). |

Alternatively, a single and identical frequency may be selected for all paths. For example, corresponding to each candidate frequency $f_m$, compute the total path number $K_m$ for which $f_m$ was selected as the best suitable actuation frequency (step 450). Let $\{K_1, K_2, \ldots, K_M\}$ be the set of these numbers. The maximum value in the set of $\{K_1, K_2, \ldots, K_M\}$, i.e., the largest value of $K_m$, may be found (step 455). Denote it by $K_{max}$ and the corresponding frequency by $f_{max}$. If $K_{max}/N$ is greater than a threshold (e.g., 90%) (a Yes result in decision block 465), then $f_{max}$ is selected (step 470) as the best suitable frequency for all the paths. Otherwise, use different actuation frequencies for each path as selected above (step 475).

Although the methods of the present invention have been described and illustrated herein with reference to certain specific example embodiments thereof, it should be understood by those of skill in this art that a wide variety of modifications and variations may be made to them without departing from the spirit and scope of the invention, as defined by the claims appended hereafter and their functional equivalents.

What is claimed is:

1. A method for optimizing performance of an array of transducers of a structural health monitoring (SHM) system, the method comprising:
    specifying a plurality of signal paths, each signal path of the plurality of signal paths respectively extending between an actuator among the transducers and a sensor among the transducers, the transducers being disposed in or on a structure;
    defining a maximum allowable propagation distance for signals traveling between the transducers;
    selecting selected paths from the plurality of signal paths based on at least the maximum allowable propagation distance and lengths of the plurality of signal paths; and,
    after the selecting, evaluating a signal quality Q of signals transmitted along the selected paths so as to optimize gain and frequency operating conditions of the transducers.

2. The method of claim 1, further comprising:
    assigning location coordinates for each of the transducers on the structure; and
    specifying candidate actuation frequencies for the plurality of signal paths,
    wherein the selecting is further based on the location coordinates.

3. The method of claim 2, wherein the evaluating of the signal quality Q comprises:
    transmitting acoustic signals along each of the selected paths using an associated actuator transducer and receiving the acoustic signals using an associated sensor transducer;
    determining optimal signal transmit and receive gains to be used for each of the selected paths;
    determining functional paths among the selected paths, based on strength levels and signal-to-noise ratios (SNRs) of the acoustic signals received using the associated sensor transducer;
    removing non-functional paths from the selected paths;
    determining an optimal operating frequency for each of the functional paths, based on the most sensitive frequency for each path of the functional paths; and,
    storing a location, optimal transmit and receive gains, and optimal operating frequency of each of the functional paths in a configuration file.

4. The method of claim 3, wherein the determining of the optimal signal transmit and receive gains for each of the selected paths comprises:
    selecting an initial signal transmitter frequency;
    setting a corresponding signal receiver filter characteristic;
    setting a transmitter gain to a selected value; and,
    setting a receiver gain to a value intermediate a minimum gain value and a maximum gain value.

5. The method of claim 4, further comprising:
    recording a received noise signal; and,
    determining a maximum received noise level in the received noise signal.

6. The method of claim 5, further comprising:
recording a received acoustic signal;
removing electromagnetic interference cross-talk from the received acoustic signal;
determining a signal level of the received acoustic signal; and,
determining a signal-to-noise ratio (SNR), wherein the SNR is the ratio of the magnitude of the received acoustic signal to the maximum received noise level.

7. The method of claim 6, further comprising:
comparing the signal level of the received acoustic signal to a maximum allowable signal level;
decreasing the receiver gain if the received acoustic signal level is greater than the maximum allowable signal level; and,
repeating the steps of claim 6 until the signal level of the received acoustic signal does not exceed the maximum allowable signal level.

8. The method of claim 6, further comprising:
comparing the SNR to a minimum signal-to-noise ratio;
increasing the transmitter gain if the SNR does not exceed the minimum signal-to-noise ratio; and,
repeating the steps of claim 6 until the SNR does exceed the selected minimum signal-to-noise ratio.

9. The method of claim 3, wherein the determining of the optimal operating frequency for each of the functional paths further comprises:
indexing the functional paths n=1, 2, ..., N, wherein N is the total number of functional paths;
indexing a set of candidate frequencies $\{f_m\}=f_1, f_2, \ldots, f_M$ for exciting signals along the selected paths, wherein M is the total number of candidate frequencies for a functional path of the functional path;
defining the signal quality Q based on the received signal level;
computing the Q for each candidate frequency $f_m$, where m=1,2, ..., M for a first path n=1;
selecting the frequency having the highest Q for the functional path of the functional paths;
repeating the computing for each path n, where n=2, ..., N; and,
storing the selected frequencies for each functional path of the functional paths.

10. The method of claim 9, further comprising:
determining the total number $K_m$ of the N functional paths having each of the candidate frequencies $f_m$, where $K_1+K_2+\ldots K_M=N$;
finding the largest $K_m=K_{MAX}$ in the set of numbers $\{K_m\}$;
designating the frequency $f_m$ corresponding to $K_m=K_{MAX}$ as $f_m=f_{MAX}$, wherein $f_{MAX}$ is the dominant frequency in the set of candidate frequencies; and,
fixing a selected threshold T between 0 and 1.

11. The method of claim 10, further comprising selecting a dominant frequency as a single transmission frequency for all N functional paths if $K_{MAX}/N>T$.

12. The method of claim 10, further comprising selecting the frequency of the signal having the highest signal quality for each functional path if $K_{MAX}/N<T$.

13. A system for optimizing actuator-sensor paths of a structural health monitoring system (SHM), comprising:
a plurality of transducers formed in an array and coupled to a structure to be monitored by the SHM system, the plurality of transducers including a plurality of transmitting transducers and a plurality of receiving transducers;
a transmit gain block comprising a waveform generator and a power amplifier;
a transmitter switch arranged to direct an output signal from the power amplifier to one of the plurality of transmitting transducers;
a receiver switch arranged to accept an input signal from one of the plurality of receiving transducers;
a receiver filter for admitting a preferred spectral content from the input signal, resulting in a filtered input signal;
a gain block for variably amplifying the filtered input signal to generate a filtered and amplified input signal;
an analog-to-digital converter (ADC) for digitizing the filtered and amplified input signal to generate a digitized input signal; and,
a computer for analyzing the digitized input signal.

14. A method for optimizing performance of a transducer array of a structural health monitoring (SHM) system having a plurality of transducers and a plurality of signal paths, the plurality of transducers including actuators and sensors, each of the plurality of signal paths respectively extending between an actuator of the transducers and a sensor of the transducers, each path having transmit and receive gains associated therewith for respectively adjusting the respective magnitudes of signals transmitted along and received from the path, the method comprising:
specifying specified paths that are elected from the plurality of signal paths;
automatically adjusting the transmit gain and the receive gain for each of the specified paths so as to improve a condition of signals transmitted along and received from the specified paths;
selecting a subset of paths from the specified paths so as to form a set of functional paths suitable for monitoring the health of a structure, the selecting being performed according to the automatically adjusted operating conditions; and,
determining a transmit frequency according to a highest value of a signal quality metric Q, the signal quality metric Q measuring quality of the signal received from a functional path among the set of functional paths.

15. The method of claim 14, further comprising:
assigning location coordinates for each of the transducers, the transducers being disposed in or on a structure;
specifying candidate actuation frequencies;
defining a maximum allowable propagation distance for signals transmitted between the transducers along the signal paths; and,
selecting an initial set of paths for signal transmissions based on the coordinate locations and the maximum propagation distance.

16. The method of claim 14, wherein the automatically adjusting of the gains comprises:
for each path of the specified paths:
determining the transmit gain according to a highest value of a signal-to-noise ratio (SNR), the SNR comparing a magnitude of a signal transmitted along the path adjusted by the transmit gain to a magnitude of noise detected from the path; and,
determining the receive gain according to a maximum amplitude $SIG_{MAX}$ of a signal received from the path.

17. The method of claim 14, wherein the determining of a transmit frequency further comprises:
selecting a set of frequencies for signals to be transmitted along each path of the functional paths;
successively transmitting signals along each path of the functional paths at each frequency of the selected set of frequencies; and,
calculating a value of Q for each signal transmitted.

18. The method of claim 17, wherein Q includes at least one of an SNR, an $SIG_{MAX}$ and a robustness defined as r=1/variance of the measured signal energy of a path collected while a selected environmental effect changes.

19. The method of claim 18, wherein the selected environmental effect comprises temperature.

* * * * *